United States Patent [19]

Warriner

[11] Patent Number: Plant 7,127

[45] Date of Patent: Jan. 30, 1990

[54] ROSE PLANT JACYIM

[75] Inventor: William A. Warriner, Tustin, Calif.

[73] Assignee: Jackson & Perkins Company, Medford, Oreg.

[21] Appl. No.: 284,132

[22] Filed: Dec. 14, 1988

[51] Int. Cl.[4] ..... A01H 5/00

[52] U.S. Cl. ..... Plt./8

[58] Field of Search ..... Plt./8

*Primary Examiner*—James R. Feyrer

*Attorney, Agent, or Firm*—Majestic, Parsons, Siebert & Hsue

[57] ABSTRACT

A rose variety of the miniature class is provided that has an abundance of bright yellow color flowers, rich glossy green foliage, a symmetrical plant habit and is resistant to powdery mildew.

1 Drawing Sheet

SUMMARY OF THE INVENTION

The present invention relates to a new and distinct variety of rose plant of the miniature class, which was originated by me by crossing the variety Rise 'n Shine with the variety Sunflare U.S. Plant Pat. No. 5,001.

The primary objective of this breeding was to produce a new rose variety of the miniature calss that possesses the characteristics of stable yellow flower color, disease resistant glossy foliage, a very uniform plant habit and very good bloom production. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. A bright yellow flower color that holds its color well;
2. Abundant disease resistant glossy foliage;
3. A very symmetrical plant and
4. Constant, high production of flowers so the plant is in bloom all through the growing season.

Asexual reproduction of this new variety by budding and by softwood cuttings, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "JACYIM". Color terminology is in accordance with The Royal Horticultural Society Colour Chart except where an ordinary dictionary significant for the color is apparent.

Observations of the buds and flowers were made from specimens grown in a greenhouse and outdoors at Somis, Calif. in May, June, October and November.

Flower

The blooming habit is continuous. The bud size is one-half to five-eighths of an inch when the petals start to unfurl. The bud form is short and pointed ovoid. The bud color when sepals first divide is near Yellow Group 10C. When half blown, the upper side and lower side of petals are near Yellow-Orange Group 21C. The sepals have a color near Yellow-Green Group 144A. The surface texture is smooth with very short tomentose hairs on the back side of each sepal. There are three normally appendaged sepals, and two unappendaged sepals with a hairy edge. The receptacle color is near Yellow-Green Group 144A and has an apple shape, large size and hairy surface. The peduncle is long and has a hairy surface. Peduncle color is light green and the peduncle is erect, bending and slender. The flower opens slowly and holds open form well.

Bloom

Blooms have an average open size of one and a half inches, borne in clusters. The clusters are flat. The stems are medium. The form when first open is flat. The outer petal edges are slightly curled towards the end. Under normal conditions there are 60 to 70 petals. The upper side and the reverse side of the petals at the flower center are both near Yellow-Orange Group 21C. The base of petals is also near Yellow-Orange Group 21C. The major color is near Yellow-Orange Group 21C. There are no variegations. The general tonality at the end of the first day is substantially the same yellow color as when fresh open. At the end of the third day, there is a slight fading of the tips of the outer petals.

There is no fragrance. The petal texture is thick. The petal shape is oval. The petal form is flat with tips slightly recurved.

The arrangement is irregular, informal and imbricated with no petaloids in the center. The blooms drop off cleanly, and last both on the plant and as a cut flower for a long time.

Reproductive Parts

The anthers are of medium size, of white color and arranged regularly around the styles. The filaments are yellow, the pollen is gold yellow, the styles are white at the base becoming pink near the stigma, and the stigmas are yellow.

Plant

The plant has very vigorous, upright growth of compact bush form which forms a round habit (that is, symmetrical) approximately two feet by two feet by two feet.

Foliage

The foliage is medium size. New foliage is green with a bronzing at shoot tips and leaf margins. Old foliage is near Green Group 139A. A normal mid-stem leaf has seven leaflets.

The leaflets have an oval pointed shape, a leathery, glossy texture on the upper side and have a serrated edge. The serration is double and small. Petiole rachis is green, with prickles on the underside. The foliage is resistant to mildew and blackspot under normal growing conditions at Wasco, Irvine and Somis, Calif.

Wood

New wood is light green in color with a smooth bark. Old wood is green with a rough bark.

Prickles

There are few prickles on the main canes from the base and on the laterals from the main canes. The prickles are long and hooked slightly downward. The prickles are red colored when young. There are no small prickles on the main stalks or laterals.

Parentage

The seed parent was of the variety Rise 'n Shine. The pollen parent was of the variety Sunflare.

Classification

Botanical is rosa hybrid. Commercial is miniature.

I claim:

1. A new and distinct variety of rose plant of the miniature class substantially as herein shown and described, characterized particularly as to novelty by the stable yellow flower color, rich glossy green foliage, outstanding globular habit, abundance of flowers and disease resistance.

* * * * *

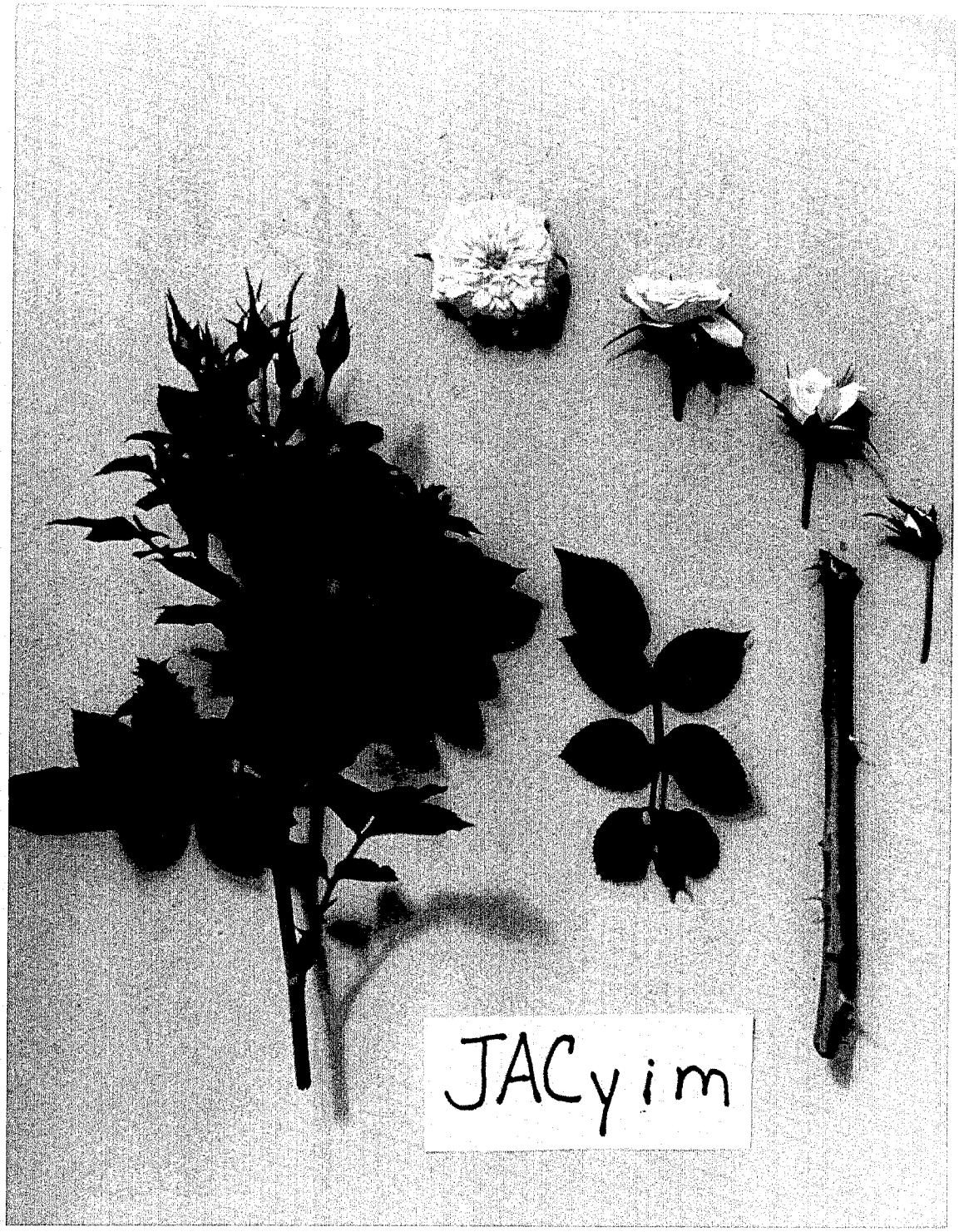
JACyim